United States Patent [19]

Avar et al.

[11] 4,146,540
[45] Mar. 27, 1979

[54] PYRAZOLE COMPOUNDS AS STABILIZERS FOR ORGANIC MATERIALS

[75] Inventors: Lajos Ávár, Biel-Benken; Kurt Hofer, Münchenstein; Martin Preiswerk, Corsier s,Vevey, Switzerland

[73] Assignee: Sandoz Ltd., Basel, Switzerland

[21] Appl. No.: 844,230

[22] Filed: Oct. 21, 1977

Related U.S. Application Data

[63] Continuation-in-part of Ser. No. 605,781, Aug. 18, 1975, abandoned, which is a continuation-in-part of Ser. No. 485,298, Jul. 2, 1974, abandoned, which is a continuation-in-part of Ser. No. 447,922, Mar. 4, 1974, abandoned.

[30] Foreign Application Priority Data

Mar. 9, 1973 [CH] Switzerland .............. 3514/73
Jun. 25, 1973 [CH] Switzerland .............. 9249/73
Jan. 9, 1974 [CH] Switzerland .............. 235/74
Aug. 15, 1975 [CH] Switzerland .............. 10713/75

[51] Int. Cl.$^2$ .............. C07F 1/00; C07F 3/00; C07F 15/00; C07D 231/22
[52] U.S. Cl. .............. 260/299; 544/64; 544/225; 544/353; 548/363; 548/364; 548/367; 546/6; 260/45.75 R; 260/45.75 C; 260/45.75 N; 260/45.75 M; 260/45.8 N
[58] Field of Search .............. 260/299, 270 K; 548/363, 364, 367, 377; 544/64, 225

[56] References Cited

U.S. PATENT DOCUMENTS

| | | | |
|---|---|---|---|
| 2,694,703 | 11/1954 | Graham | 260/163 |
| 3,074,909 | 1/1963 | Matlack | 260/45.75 |
| 3,808,228 | 4/1974 | Trofimenko | 260/310 R |
| 3,959,265 | 5/1976 | Avar et al. | 260/242 |
| 3,963,737 | 6/1976 | Avar et al. | 260/299 |
| 4,008,200 | 2/1977 | Avar et al. | 260/45.75 N |
| 4,036,631 | 7/1977 | Konotsune et al. | 71/92 |
| 4,063,925 | 12/1977 | Konotsune et al. | 71/92 |
| 4,070,536 | 1/1978 | Konotsune et al. | 548/367 |

FOREIGN PATENT DOCUMENTS

| | | |
|---|---|---|
| 812018 | 9/1974 | Belgium. |
| 817388 | 1/1975 | Belgium. |
| 2513750 | 10/1975 | Fed. Rep. of Germany. |
| 2220565 | 10/1974 | France. |
| 111396 | 2/1975 | German Democratic Rep. |

OTHER PUBLICATIONS

Jenson, Chemical Abstracts, vol. 57, 382a (1962).
Zolotov et al., Chemical Abstracts, vol. 64, 2801d (1966).
Mirza, Chemical Abstracts, vol. 68, 34,952f (1968).
Suenaga, Chemical Abstracts, vol. 53, 13,136f (1959).
Mirza et al., Chemical Abstracts, vol. 70, 91,285f (1969).
Zolotov et al., Chemical Abstracts, vol. 71, 129,385z (1969).
Navratil et al., Chemical Abstracts, vol. 76, 7122u (1972).

*Primary Examiner*—Donald G. Daus
*Assistant Examiner*—Diana G. Rivers
*Attorney, Agent, or Firm*—Gerald D. Sharkin; Richard E. Vila; Joseph J. Borovian

[57] ABSTRACT

The present invention concerns certain novel compounds falling under the general formula:

$$R_3 \text{—} \underset{\underset{R_1}{N}}{\overset{N}{\diagdown}} \text{—} \overset{O}{\underset{\|}{C}} \text{—} R_2 \text{, OMe}$$

wherein $R_1$, $R_2$ and $R_3$ are substituents, e.g. alkyl and Me is hydrogen or a metal cation.

The compounds are useful stabilizers of organic material against the degradative effect of heat, oxidation and U.V. light.

23 Claims, No Drawings

PYRAZOLE COMPOUNDS AS STABILIZERS FOR ORGANIC MATERIALS

The present application is a continuation-in-part of our copending application Ser. No. 605,781, filed Aug. 18, 1975, and now abandoned which itself is a continuation-in-part of our application Ser. No. 485,298, filed July 2, 1974, and now abandoned, which itself is a continuation-in-part of our application Ser. No. 447,922, filed Mar. 4, 1974, and now abandoned.

The present invention relates to pyrazole compounds useful as stabilizers against heat, oxidation or ultraviolet light.

Accordingly, the present invention provides a method of stabilizing organic material susceptible to degradation under the effect of heat, oxidation or ultraviolet light which comprises treating said material with a compound of formula I,

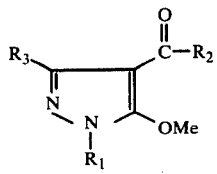

wherein $R_1$ is alkyl ($C_1$–$C_{22}$); cycloalkyl ($C_5$–$C_{12}$); cycloalkyl ($C_5$–$C_{11}$) alkyl ($C_1$–$C_7$); alkyl ($C_1$–$C_{21}$) thioalkyl ($C_1$–$C_{21}$) with $C_2$–$C_{22}$ in the aggregate thereof; cycloalkyl ($C_5$–$C_{11}$) alkyl ($C_1$–$C_6$) thioalkyl ($C_1$–$C_6$) with $C_7$–$C_{18}$ in the aggregate thereof; aralkyl ($C_7$–$C_{12}$); aralkyl ($C_7$–$C_{12}$) substituted on the aryl nucleus by 1 or 2 hydroxyl groups, 1 or 2 alkyl ($C_1$–$C_{12}$) groups, cycloalkyl ($C_5$–$C_{12}$) and/or cycloalkyl ($C_5$–$C_{11}$) alkyl ($C_1$–$C_{11}$); phenyl; phenyl substituted by 1 to 3 halogen atoms, cyano, 1 or 2 hydroxyl groups, 1 or 2 alkyl ($C_1$–$C_{12}$) groups, 1 or 2 alkoxy ($C_1$–$C_{12}$) groups, phenyl, —$SO_3H$ and/or a radical $R_4$—O— or $R_4$—$SO_2$—, wherein $R_4$ is phenyl or phenyl substituted by 1 or 2 alkyl ($C_1$–$C_8$) groups;

$R_2$ has one of the significances of $R_1$ or is a furan, thiophene, benzothiophene, indole, pyridine or quinoxaline radical, each of which is either unsubstituted or substituted by halogen, alkyl ($C_1$–$C_4$) and/or alkoxy ($C_1$–$C_4$) with 1 or 2 substituents in the aggregate thereof;

$R_3$ has one of the significances of $R_1$ or is cyano or —$COOR_5$, wherein $R_5$ is alkyl ($C_1$–$C_{12}$), cycloalkyl ($C_5$–$C_{12}$), cycloalkyl ($C_5$–$C_{11}$) alkyl ($C_1$–$C_7$), phenyl or phenyl substituted by hydroxy and/or 1 to 2 alkyl ($C_1$–$C_8$) groups, and Me is hydrogen or an equivalent of a bivalent metal ion.

A preferred group of compounds in the method of the invention are the compounds of formula Ia,

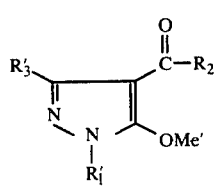

wherein $R_1'$ and $R_3'$, are each independently, alkyl ($C_1$–$C_8$), phenyl or phenyl substituted by halogen and/or 1 or 2 alkyl ($C_1$–$C_4$) groups, Me' is hydrogen or an equivalent of nickel, zinc, manganese, copper, chromium, calcium, barium or cobalt, and $R_2$ is as defined above.

A further preferred group of compounds in the method of the invention are the compounds of formula Ib,

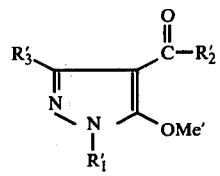

wherein $R_2'$ is alkyl ($C_6$–$C_{18}$); cycloalkyl ($C_6$–$C_8$); aralkyl ($C_7$–$C_{10}$); aralkyl substituted on the aryl nucleus by hydroxyl and/or 1 or 2 alkyl ($C_1$–$C_6$) groups; phenyl; phenyl substituted by 1 to 3 halogen atoms, 1 or 2 hydroxyl groups, 1 or 2 alkyl or alkoxy ($C_1$–$C_8$) groups and/or phenyl; a furan, thiophene or benzothiophene radical, unsubstituted or substituted by halogen and/or alkyl ($C_1$–$C_4$), with 1 or 2 substituents in the aggregate thereof, and $R_1'$, $R_3'$ and Me' are as defined above.

A further preferred group of compounds in the method of the invention are the compounds of formula Ic,

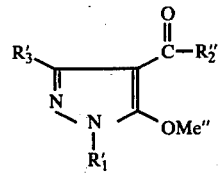

wherein $R_2''$ is alkyl ($C_8$–$C_{18}$); cycloalkyl ($C_6$–$C_8$); aralkyl ($C_7$–$C_{10}$); aralkyl substituted on the aryl nucleus by a hydroxyl and/or 1 or 2 alkyl ($C_1$–$C_6$) groups; phenyl; phenyl substituted by 1 or 2 halogen, hydroxyl, 1 or 2 alkyl or alkoxy ($C_1$–$C_8$) groups and/or phenyl with 1 to 3 substituents in the aggregate thereof; or a furan, thiophene or benzothiophene radical unsubstituted or substituted by 1 or 2 halogens or alkyl ($C_1$–$C_4$);

Me'' is nickel, zinc, manganese, copper, chromium or cobalt, and $R_1'$ and $R_3'$ are as defined above.

A further preferred group of compounds in the method of the invention are the compounds of formula Id,

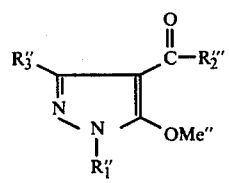

wherein $R_1''$ is phenyl, phenyl substituted by alkyl ($C_1$-$C_4$) or methyl, $R_3''$ is alkyl ($C_1$-$C_4$) or phenyl, $R_2'''$ is alkyl ($C_8$-$C_{11}$); cyclohexyl; phenylethyl; phenylethyl substituted on the phenyl nucleus by a hydroxyl group, and/or 1 or 2 alkyl ($C_1$-$C_4$) groups; phenyl; phenyl substituted by hydroxyl, 1 or 2 alkyl ($C_1$-$C_4$) groups, alkoxy ($C_1$-$C_4$) and/or phenyl with 1 to 3 substituents in the aggregate thereof; or a furan, thiophene or benzothiophene radical unsubstituted or substituted by chlorine, methyl or ethyl with 1 or 2 substituents in the aggregate thereof, and Me" is as defined above.

The invention also provides compounds of formula Ie,

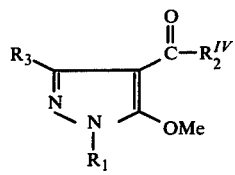

wherein $R_2^{IV}$ is alkyl ($C_8$-$C_{18}$) especially ($C_8$-$C_{13}$); a cycloalkyl ($C_6$-$C_{12}$); aralkyl ($C_7$-$C_{10}$); aralkyl substituted on the aryl nucleus by hydroxyl and/or 1 or 2 alkyl ($C_1$-$C_6$) groups; phenyl; phenyl substituted by 1 or 2 halogens, a hydroxyl, 1 or 2 alkyl or alkoxy ($C_1$-$C_8$) groups and/or phenyl with 1 to 3 substituents in the aggregate thereof and when exclusively substituted by halogen, and Me is hydrogen, then the phenyl has 2 halogen substituents; a furan, thiophene, benzothiophene, indole, pyridine or quinoxaline radical, unsubstituted or substituted by 1 or 2 halogen atoms, or 1 or 2 alkyl or alkoxy ($C_1$-$C_4$) groups with 1 or 2 substituents in the aggregate thereof, and $R_1$, $R_3$ and Me are as defined above.

Examples of interesting groups of compounds within the scope of formula I are the compounds of formula If,

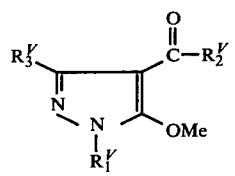

wherein $R_1^V$ is alkyl ($C_1$-$C_6$), phenyl or phenyl substituted by alkyl ($C_1$-$C_4$), $R_2^V$ is alkyl ($C_1$-$C_{20}$), e.g. ($C_8$-$C_{18}$); cyclohexyl; phenyl or phenylethyl, unsubstituted or substituted on the phenyl nucleus by 1 or 2 alkyl ($C_1$-$C_4$) groups, an alkoxy ($C_1$-$C_4$) group, a hydroxyl group and/or a phenyl group and bearing 1 to 3 substituents in the aggregate, a thiophene radical unsubstituted or substituted by an alkyl ($C_1$-$C_4$) group or chlorine atom, or a quinoxaline radical unsubstituted or disubstituted on the hetero ring thereof by chlorine, $R_3^V$ is alkyl ($C_1$-$C_4$) or phenyl and Me is as defined above, e.g. compounds of formula Ig,

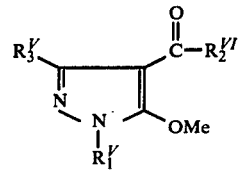

wherein $R_1^V$, $R_3^V$ and Me are as defined above and $R_2^{VI}$ is alkyl ($C_1$-$C_{20}$), compounds of formula Ih,

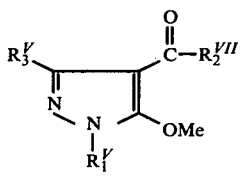

wherein $R_1^V$, $R_3^V$ and Me are as defined above and $R_2^{VII}$ is phenyl or phenylethyl, unsubstituted or substituted on the phenyl nucleus by 1 or 2 alkyl ($C_1$-$C_4$) groups, an alkoxy ($C_1$-$C_4$) group, a hydroxyl group and/or a phenyl group, the compounds of formula Ii,

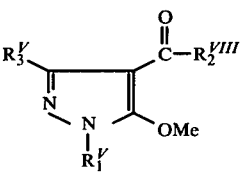

wherein $R_1^V$, $R_3^V$ and Me are as defined above and $R_2^{VIII}$ is a thiophene radical, unsubstituted or substituted by an alkyl ($C_1$-$C_4$) group or a chlorine atom; and the compounds of formula Ij,

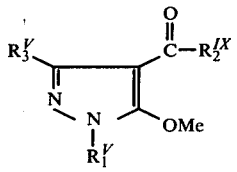

wherein $R_1^V$, $R_3^V$ and Me are as defined above and $R_2^{IX}$ is quinoxaline unsubstituted or disubsubstituted on the hetero ring thereof by chlorine.

Amongst the preferred compounds of formula Ie are the compounds of formula Ie',

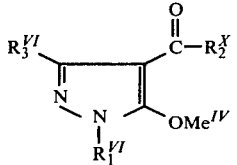

wherein $R_1^{VI}$ is phenyl or phenyl substituted by alkyl ($C_1$-$C_4$), $R_2^X$ is alkyl ($C_8$–$C_{17}$), phenyl, phenylethyl or phenyl or phenylethyl substituted on the phenyl nucleus by 1 or 2 alkyl ($C_1$–$C_4$) groups and/or by hydroxyl, $R_3$ is alkyl ($C_1$–$C_4$) and $Me^{IV}$ is H or one equivalent of Ni or Mn.

The compounds of formulae Ie, Ie′, If, Ig, Ih, Ii and Ij are preferably in substantially pure form, i.e. at least 90%, more preferably at least 95%, especially 97–100%, and in particular 98 to 100% by weight, excluding water of crystallization.

When in substantially pure form, the metal complex forms thereof at least are crystalline solids which may be ground into powders.

The compounds of formulae Ie, Ie′, If, Ig, Ih, Ii and Ij are preferably in metal complex form, i.e. Me is preferably a metal cation.

By the term "halogen" as used herein is meant chlorine and bromine.

Alkyl radicals, unless otherwise stated, are natural or synthesizable primary, secondary or tertiary, straight or branched chain radicals. Examples of primary radicals are methyl, ethyl, n-propyl, n-butyl, n-pentyl, n-hexyl, n-heptyl, n-octyl, n-nonyl, n-undecyl, n-dodecyl, n-hexadecyl, n-heptadecyl, n-octadecyl and n-docosanyl.

Examples of secondary alkyl radicals are isopropyl, 2-butyl, 3-methyl-2-butyl, 2-pentyl, 2-hexyl, 3-hexyl, 2-methyl-3-pentyl, 3-octyl, 4-octyl, 2-decyl, 5-decyl, 2,2-dimethyl-3-octyl, 2-heptadecyl, 2-hexadecyl and 2-nonadecyl.

Examples of tertiary alkyl radicals are tertiary butyl, 3-methyl-3-hexyl, 1-methyl-cyclohexyl and tertiary octyl.

Examples of branched alkyl radicals are 2-methyl-1-propyl, 2,2-dimethyl-1-propyl, 2-methyl-1-butyl, and 2,2-dimethyl-1-decyl.

Examples of cycloalkyl radicals are cyclopentyl, cyclohexyl, cycloheptyl, 2-, 3- or 4-methylcyclohexyl, cyclooctyl and cyclododecyl.

The term "cycloalkyl" as used herein includes a cycloalkyl ring bearing alkyl substituents.

Examples of cycloalkylalkyl are cyclohexylmethyl, cyclohexyl-ethyl and cycloheptyl-methyl.

Examples of aralkyl radicals are benzyl and 2-phenylethyl.

Examples of radicals, where the aliphatic chain is interrupted by sulphur are 2-methylthioethyl, 2-dodecylthioethyl and methyl-thiomethyl.

Examples of substituted phenyl radicals are:

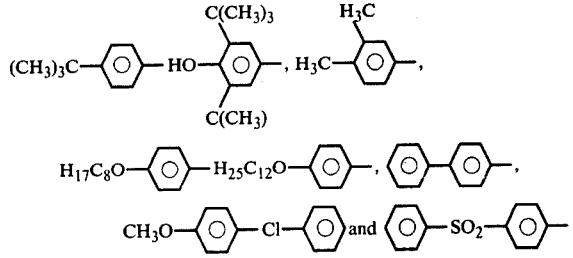

Examples of unsubstituted and substituted furan, thiophene, benzothiophene, indole, pyridine and quinoxaline radicals are:

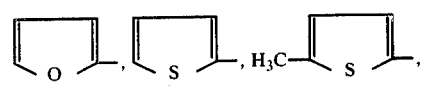

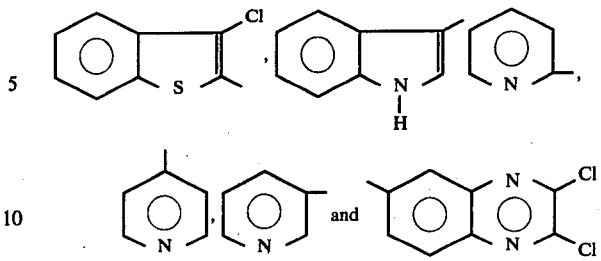

The present invention also provides a process for producing a compound of formula Ie, which comprises condensing a compound of formula III,

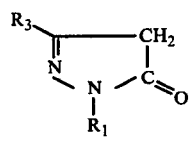

wherein $R_1$ and $R_3$ are as defined above, with a compound of formula II, $$R_2^{IV} COCl \qquad \qquad II$$

wherein $R_2^{IV}$ is as defined above, preferably in an equimolar ratio and, when Me signifies an equivalent of a metal ion, converting the resulting product into the corresponding Me− salt.

The reaction is preferably effected in an inert organic solvent and the starting materials may be dissolved or suspended therein. The solution is preferably heated to between 20° and 110° C. with the cleavage of hydrochloric acid which may be allowed to escape from the reaction vessel at an elevated temperature. Generally, it is, however, more convenient to effect the reaction in the presence of an acid binding agent, e.g. CaO, an alkali metal carbonate or bicarbonate, pyridine, a trialkyl amine or a dialkyl aniline. The reaction is preferably carried out in the absence of moisture. Appropriate solvents are, for example, benzene, xylene, cymol, diphenyl ether, tetrahydrofuran and dioxane. When Me signifies a bivalent metal ion, the compound of formula I, wherein Me signifies hydrogen, may be converted first into the alkali metal salt, e.g. by dissolving the compound of formula I in alcohol and adding an alkali hydroxide such as NaOH or KOH. A Me− salt, e.g. the chloride, is subsequently added to the reaction mixture and the desired product is then obtained.

Alternatively and preferably, a metal salt may be produced directly from the compound of formula I, wherein Me signifies hydrogen, by heating the compound of formula I wherein Me is hydrogen with an Me− acetate, e.g. the acetate of nickel, zinc, manganese, cobalt, copper, calcium or barium. This reaction is preferably effected in an alcohol such as methanol, ethanol and propanol, at a temperature between room temperature and the reflux temperature of the solvent. On cooling the product generally precipitates.

If the product does not precipitate sufficiently, the precipitation may be accelerated by the addition of water.

The compounds of formula I are useful for stabilizing organic material susceptible to degradation under the effect of heat, oxidation or U.V. light by a method comprising treating the organic material with a compound of formula I. By the term "treating" is meant either surface coating or incorporation into the body of the organic material, in manner known per se.

The above method also forms part of the present invention.

The method of the invention comprises treating the organic material, either by way of coating the compound of formula I as a film on the surface of the organic material, or by way of mixing the compound of formula I with the organic material, preferably the latter so as to uniformly distribute the compound of formula I throughout the body of the organic material. Thus, according to a first embodiment the method may be effected by intimately mixing the stabilizer with a particulate form of, for example, a plastics material such as polypropylene, e.g. polypropylene granules, in a kneader or other suitable device, to obtain uniform distribution of the stabilizer throughout the plastics material. The plastics material may thereafter be formed into final shape, e.g. by extrusion or injection moulding. By such method, homogeneous distribution of the stabilizer throughout the plastics material is achieved which is important for good protection.

According to a second embodiment, organic material in final form, for example, a textile filament, is passed through a dispersion of the stabilizer, e.g. in aqueous medium, to provide a protective coating of the stabilizer as a surface film on the organic material. Textile filaments or fabrics of polyethylene terephthalate or cellulose acetate are suited to this mode of application.

According to a third embodiment of the method of the present invention, particularly suited to stabilization of polymers or copolymers, e.g. polypropylene, the stabilizer is mixed with the monomer or prepolymer before polymerisation or, as the case may be, copolymerisation, is effected, to yield the polymer or copolymer having the stabilizer uniformly distributed therethrough. The polymer or copolymer may thereafter be extruded, moulded or otherwise formed into final shape.

Examples of organic materials susceptible to degradation and embraced by the method of the present invention are cellulose derivates, e.g. cellulose acetate, cellulose acetobutyrate, ethyl cellulose, cellulose nitrate and cellulose propionate, polyalkylenes, notably polyethylene and polypropylene, polyvinyl derivatives, e.g. polyvinyl chloride, polyvinyl chloride acetate and polyvinyl alcohol, polyamides, polyesters, polyacrylonitrile, polystyrene, silicon rubber, melamineformaldehyde resins, urea-formaldehyde resins, allyl casting resins, polymethylmethacrylate, polypropylene oxide, polyphenylene oxide polyurethanes, copolymers such as acrylonitrile - butadiene - styrene copolymers and natural products such as natural rubber, cellulose, wool and silk.

The compounds according to the invention are preferably used for the stabilization of polypropylene, polyethylene, polyester, polyamide, polyurethanes, polyacrylonitrile, copolymers such as acrylonitrile-butadiene-styrene (ABS) terpolymer, acrylicester-styrene-acrylonitrile terpolymer, styrene-acrylonitrile copolymer or styrene-butadiene copolymer.

Stabilized organic materials according to the invention may exist in solid form, e.g. panels, rods, coatings, sheets, films, tapes, fibres, granules or powders, or in liquor form, e.g. solutions, emulsions or dispersions.

The amount of stabilizer employed in the method of the present invention will of course vary with the mode of application, the compound employed and the nature of the organic material to be treated. In general, however, satisfactory results are obtained when the amount of stabilizer employed is between 0.01 and 5%, preferably between 0.05 and 1% of the weight of organic material to be treated.

The compounds of formula I may be employed in formulation form for the stabilization of organic materials, in association with an inert carrier or diluent. Such formulations may be in the form of polishes, creams and lotions, e.g. for surface application to the organic material so as to form a barrier or filter coating. Such formulations also form part of the present invention.

In the following Examples the parts and percentages are by weight and the temperatures in degrees Centigrade. The indicated structures are verified by microanalysis and spectroscopic analysis.

EXAMPLE 1

A mixture of 17.4 parts of 1-phenyl-3-methyl-pyrazolone (5), 11.2 parts of CaO and 19.6 parts of 4-tert.butyl-benzoyl chloride is boiled at reflux in 100 parts of dioxane over the course of 30 minutes. The obtained thick slurry is poured into 200 parts of water, at room temperature and with stirring. The resulting brown solution is acidified with diluted hydrochloric acid, the precipitate is filtered by suction, washed to neutral, dried and crystallized from methanol. The compound of formula

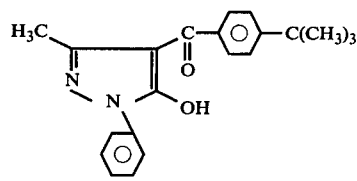

is obtained. M.P.: 107°–109° C. The estimated purity of the product was 98–100%.

In order to produce the nickel salt, 10 parts of the resulting compound are dissolved in 20 parts of methanol and the stoichiometric amount of nickel acetate is added. The mixture is then heated to 70° C. over the course of 30 minutes and allowed to cool. The green precipitate is filtered by suction, washed with methanol/water 1:1 and dried at 110° C. M.P.: 205° C. A practically quantitative yield is obtained. The estimated purity of the product was 98–100%. The salts of zinc, manganese, cobalt, copper, calcium or barium are obtained by analogy.

EXAMPLE 2

A mixture of 8.26 parts of 1,3-diphenyl-pyrazolone (5), 3.92 parts of CaO and 9.38 parts of 3,5-di-tert.butyl-4-hydroxybenzoyl chloride is boiled at reflux in 100 parts of dioxane over the course of 2 hours. The mixture is subsequently cooled to room temperature and poured into a solution consisting of 50 parts of 2n hydrochloric acid and 100 parts of ice water. The precipitate is filtered by suction, washed until neutral and crystallized from methanol. The compound of formula

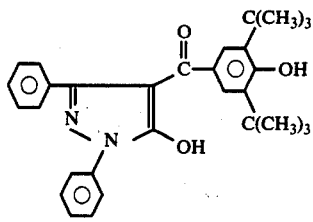

is obtained. M.P.: 187°–188° C.

The estimated purity of the product was 98–100%.

The nickel salt may be produced in analogy with Example 1.

EXAMPLE 3

3.75 Parts of 1,3-diphenyl-4[3',5'-di-tert.butyl-4'-hydroxy] benzoyl-5-hydroxy-pyrazole are entered into 60 parts of ethanol and the mixture is heated to 45°. 4 Parts of 2n sodium hydroxide solution are added at the same temperature. After 10 minutes a solution of 0.94 parts of $NiCl_2$—$6H_2O$ in 20 parts of ethanol is added to the mixture. The solution immediately turns green and KCl is precipitated. After 30 minutes of reaction the KCl is filtered off and the green solution evaporated. The solid residue is washed with water, filtered by suction and dried at 120°. The compound of formula

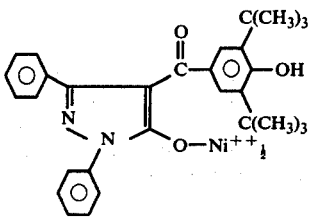

is obtained. M.P.: 250° C. The estimated purity of the product was 98–100%.

EXAMPLE 4

34.8 Parts of 1-phenyl-3-methyl-pyrazolone (5) and 13.2 parts of CaO are entered at room temperature into 40.0 parts of dioxane. The mixture is then heated to 80° C. in an oil bath. 43.7 Parts of lauric acid chloride are added dropwise at 75° C. with stirring. The acid chloride is added over the course of 45 minutes. The temperature is raised to 95° C. and a thick, brown well stirrable paste is obtained. After the addition of the acid chloride the mixture is allowed to react at 80° C. for 1 hour and is then cooled to 50° C. 100 cc of methanol and 23.0 parts of hydrochloric acid are successively added. After the addition of the hydrochloric acid the mixture is stirred for 30 minutes and 24.8 parts of nickel acetate are added. The mixture is stirred at reflux for 30 minutes. (internal temperature: 70° C.). The precipitated nickel complex is filtered by suction at 50° C., washed until free from halogen with 1,5 parts of water and then washed twice with 30 parts of methanol each time and dried at 110° C. M.P.: 144°–148° C. The nickel salt, i.e. the compound of formula

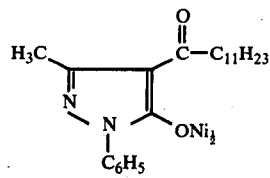

is obtained, having an estimated purity of 98–100%.

The corresponding zinc, cobalt, manganese, copper, calcium or barium complex is produced in analogy with Example 1 or 3.

EXAMPLE 5

A mixture of 53.3 g of 1-phenyl-3-methyl-pyrazolone (5), 18.5 g of CaO and 44.0 g of thiophene-2-carboxylic acid chloride is stirred in 120 cc of dioxane at 95° C. over the course of 2 hours. After cooling to 50° C., 100 cc of methanol and 30 cc of concentrated hydrochloric acid are successively added. The mixture is then stirred for a further 30 minutes. The mixture is then poured into 500 cc of ice water, whereupon a voluminous precipitate is obtained. The precipitate is filtered by suction, washed with water and crystallized from methanol. M.P.: 133°–136° C. The compound of formula

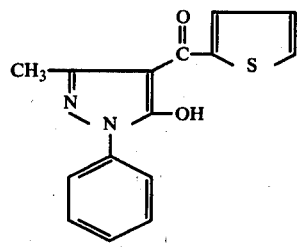

is obtained, having an estimated purity of 98–100%.

EXAMPLE 6

A mixture consisting of 20.2 g of 1-phenyl-3-n-propyl-pyrazolone (5) and 6.2 g of CaO is heated to 75° C. in 80 cc of dioxane; 14.7 g of thiophene-2-carboxylic acid chloride are added with stirring at the same temperature over the course of 15 minutes, whereupon the reaction temperature rises to 95° C. The mixture is allowed to react at 95° C. for 1 hour and the dioxane is subsequently distilled off. To the resulting thick, brown slurry are added 100 cc of methanol and 10 cc of concentrated hydrochloric acid and the mixture is kept under reflux for 30 minutes. The obtained clear, brown solution is poured on 200 cc of ice water. The reaction product precipitates. The precipitate is filtered by suction, washed with water and crystallized from ethanol. M.P.: 124°–128° C. The compound of formula

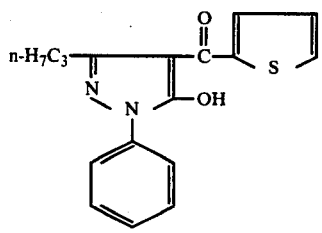

is obtained, having an estimated purity of 98–100%.

EXAMPLE 7

5.0 g of Nickel acetate 6H$_2$O are added at 45° C. to 12.5 g of the compound of Example 6 in 100 cc of methanol. The mixture is stirred for 1 hour without further heating. The green precipitate is filtered by suction, washed with water and dried at 90° C. M.P.: 145°–155° C. The compound of formula

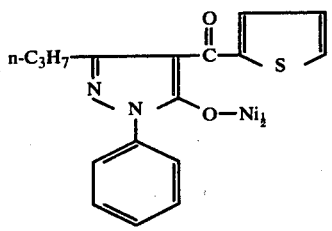

is obtained, having an estimated purity of 98–100%.

EXAMPLE 8

To 18.8 g of 1-p-tolyl-3-methyl-pyrazolone (5) and 6.18 g of CaO in 100 cc of dioxane there are added with stirring at 90° C. over the course of 30 minutes 14.7 g of thiphene-2-carboxylic acid chloride. The dioxane is subsequently distilled off in a water-jet vacuum 80 cc of methanol and 10 cc of concentrated hydrochloric acid are added at 60° C. to the resulting thick paste which is boiled under reflux over the course of 30 minutes. 11.8 g of Nickel acetate 6H$_2$O are then added, the mixture is stirred for a further 30 minutes and subsequently cooled to room temperature. The green precipitate is filtered by suction, washed with water and dried. M.P.: 180°–184° C. The compound of formula

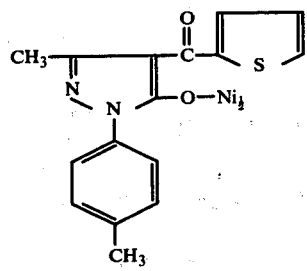

is obtained, having an estimated purity of 98–100%.

EXAMPLE 9

A solution of 1.6 g of NaOH in 10 cc of water is added at 45° C. to 11.4 g of the compound of Example 5 in 100 cc of methanol and the mixture is stirred for 30 minutes. 4.6 g of NiCl$_2$.6H$_2$O, dissolved in 20 cc of water, are then added to the yellow solution. After the addition of the nickel chloride a green precipitate is obtained which is filtered by suction at room temperature, washed with water and dried. M.P.: 175°–180° C. The compound of formula

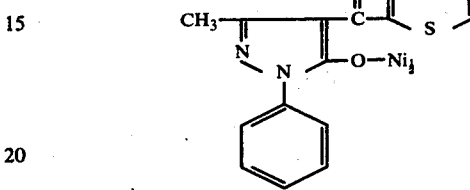

is obtained, having an estimated purity of 98–100%.

EXAMPLE 10

5.0 g of Cobalt (II)acetate are added with stirring at 45° C. to 11.4 g of the compound of Example 5 in 150 cc of methanol. After the addition of the salt a precipitate is obtained. The yellow precipitate is filtered by suction at room temperature, washed with water and dried. M.P.: 165°–170° C. The compound of formula

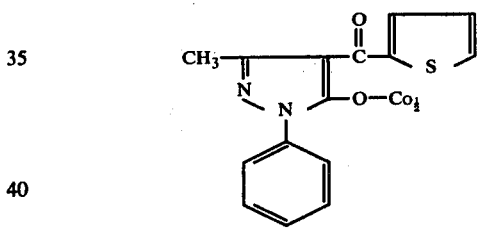

is obtained, having an estimated purity of 98–100%.

The compounds indicated in Tables 1,2,3,4,5,6 and 7 are produced in analogous manner to that described in Examples 1 to 10. The estimated purities given do not take account of any water of crystallization in the case of crystalline compounds, i.e. any such water present is not counted as an "impurity".

Table 1

| Ex. No. | R$_1$ | R$_3$ | R$_2$ | Melting Point | Estimated Purity % |
|---|---|---|---|---|---|
| 11 | phenyl | CH$_3$ | 4-methoxyphenyl | 157–159° | 98–100 |
| 12 | phenyl | CH$_3$ | biphenyl | 147–149° | 98–100 |

Table 1-continued

[structure: pyrazole with R3 at 3-position, CO-R2 at 4-position, OH at 5-position, N-R1]

| Ex. No. | R₁ | R₃ | R₂ | Melting Point | Estimated Purity % |
|---|---|---|---|---|---|
| 13 | phenyl | CH₃ | 3,5-di-tert-butyl-4-hydroxyphenyl | 150–152° | 95–98 |
| 14 | phenyl | CH₃ | —CH₂—CH₂—(3,5-di-tert-butyl-4-hydroxyphenyl) | 109–110° | 95–98 |
| 15 | phenyl | CH₃ | 2-OCH₃-3-C(CH₃)₃-5-C(CH₃)₃-phenyl | Resin | 90–95 |
| 16 | phenyl | CH₃ | —C₈H₁₇(n) | Oil | 90–95 |
| 17 | phenyl | CH₃ | —C₁₇H₃₅(n) | 45–47° | 98–100 |
| 18 | phenyl | CH₃ | phenyl | 114–115° | 98–100 |
| 19 | phenyl | phenyl | 4-CH₃-phenyl | 193–194° | 98–100 |
| 20 | phenyl | phenyl | 4-C(CH₃)₃-phenyl | 134–136° | 98–100 |
| 21 | phenyl | phenyl | —C₈H₁₇(n) | 59–61° | 98–100 |
| 22 | phenyl | phenyl | —CH₂CH₂—(3,5-di-tert-butyl-4-hydroxyphenyl) | 106–109° | 95–98 |
| 23 | phenyl | phenyl | n-C₁₁H₂₃ | 69–70° | 98–100 |

Table 1-continued
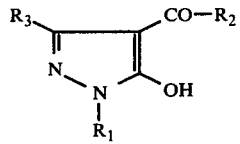
| Ex. No. | $R_1$ | $R_3$ | $R_2$ | Melting Point | Estimated Purity % |
|---|---|---|---|---|---|
| 24 | $CH_3$ | $CH_3$ |  | 132–135° | 95–98 |
| 25 | 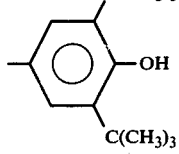 | $CH_3$ | H | 77–78° | 98–100 |
| 26 | 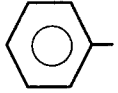 |  |  | 100–101° | 98–100 |
| 27 | 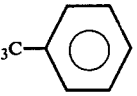 | $CH_3$ |  | 127–130° | 98–100 |
| 28 | " | " |  | 165–166° | 98–100 |
| 29 |  | " | $-C_9H_{19}(n)$ | 44° | 98–100 |
| 30 | $CH_3$ | " |  | 132–135° | 95–98 |
| 31 | 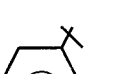 | " | 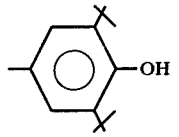 | 190–191° | 98–100 |
Table 2
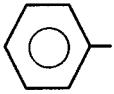
| Ex. No. | $R_3$ | $R_2$ | Me | Melting Point | Estimated Purity % |
|---|---|---|---|---|---|
| 32 | $CH_3$ | 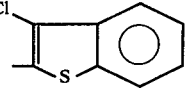 | Ca | >250° | 95–98 |
| 33 | $CH_3$ | 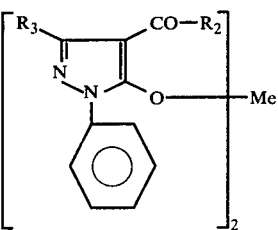 | Ni | >200° | 98–100 |

Table 2-continued
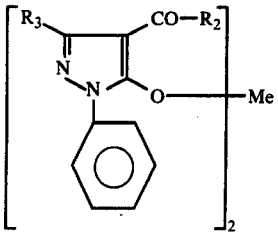
| Ex. No. | R₃ | R₂ | Me | Melting Point | Estimated Purity % |
|---|---|---|---|---|---|
| 34 | CH₃ |  | Mn | ~180° | 98–100 |
| 35 | CH₃ | 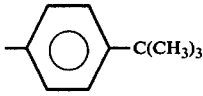 | Cu | >250° | 95–98 |
| 36 | CH₃ | 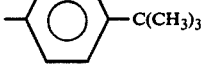 | Ca | >200° | 95–98 |
| 37 | CH₃ |  | Ni | 227–240° | 98–100 |
| 38 | CH₃ |  | Cu | >250° | 98–100 |
| 39 | CH₃ | 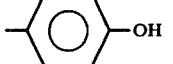 | Ni | >260° | 95–98 |
| 40 | CH₃ | 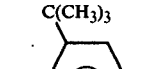 | Cu | >250° | 95–98 |
| 41 | CH₃ | 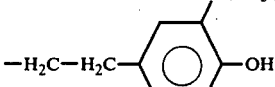 | Mn | >230° | 90–95 |
| 42 | CH₃ | —C₈H₁₇(n) | Ni | 150–170° | 98–100 |
| 43 | CH₃ | 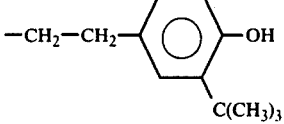 | Ni | 180–190° | 95–98 |
| 44 | CH₃ |  | Cu | 110–130° | 95–98 |

Table 2-continued
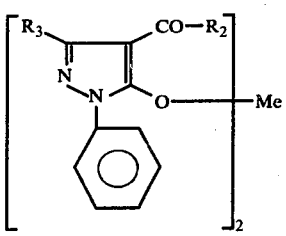
| Ex. No. | $R_3$ | $R_2$ | Me | Melting Point | Estimated Purity % |
|---|---|---|---|---|---|
| 45 | $CH_3$ | 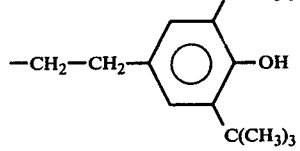 | Zn | 163–183° | 95–98 |
| 46 | $CH_3$ |  | Ni | 230–240° | 98–100 |
| 47 | $CH_3$ |  | Mn | >250° | 98–100 |
| 48 | $CH_3$ | 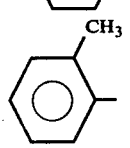 | Mn | 180–200° | 98–100 |
| 49 | $CH_3$ | 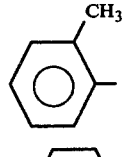 | Zn | 190–210° | 95–98 |
| 50 | $CH_3$ | 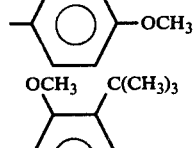 | Ni | 195° | 98–100 |
| 51 | $CH_3$ | 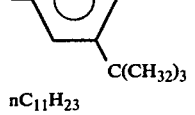 | Ni | 115–120° | 90–95 |
| 52 | $nC_3H_7-$ | $nC_{11}H_{23}$ | Ni | 164–169° | 98–100 |
| 53 | 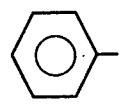 | $C_8H_{17}(n)$ | Ni | ~170° | 98–100 |
| 54 | 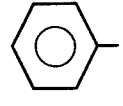 | $C_{11}H_{23}(n)$ | Ni | ~170 | 98–100 |
| 55 | 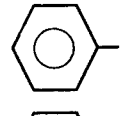 | $nC_{11}H_{23}$ | Mn | ~110 | 90–95 |
| 56 | 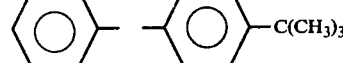 | | Zn | 200–220° | 90–95 |
| 57 | " | " | Mn | 200–215° | 90–95 |
| 58 | " | " | Cu | >250° | 90–95 |

Table 2-continued
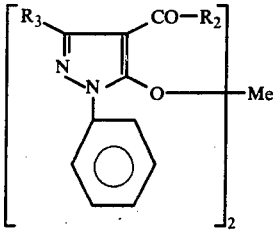
| Ex. No. | R₃ | R₂ | Me | Melting Point | Estimated Purity % |
|---|---|---|---|---|---|
| 59 | " | 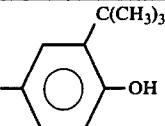 | Ni | 148–150° | 95–98 |
| 60 | " | 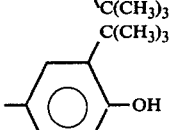 | Mn | 147–149° | 95–98 |
| 61 | " | " | Zn | 143–145 | 95–98 |
| 62 | " | " | Mn | 185–190° | 95–98 |
| 63 | " | 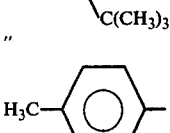 | Ni | ~150° | 95–98 |
| | | 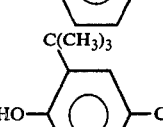 | | | |
| 64 | CH₃ | 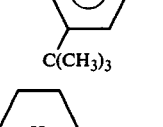 | Ni | ~175° | 98–100 |
| 65 | " | " | Co | ~190° | 98–100 |
| 66 | " | " | Zn | ~180° | 95–98 |
| 67 | CH₃ |  | Mn | ~180° | 95–98 |
| 68 | " | $C_{13}H_{27}$ | Ni | ~150° | 98–100 |
| 69 | " | $C_{15}H_{31}$ | Ni | ~150° | 98–100 |
| 70 | " | $C_{17}H_{35}$ | Ni | ~150° | 98–100 |
Table 3
| Ex. No. | R₁ | R₃ | R₂ | Me | Melting Point | Estimated Purity % |
|---|---|---|---|---|---|---|
| 71 |  | —CH₃ |  | Co | >200° | 98–100 |
| 72 | " | 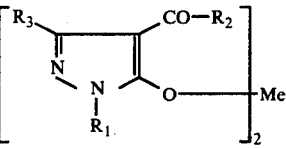 | —C₁₁H₂₃ | Co | ~125° | 98–100 |

Table 3-continued $$\left[\begin{array}{c}R_3 \quad CO-R_2 \\ \diagdown \\ N \\ | \\ N \\ | \\ R_1\end{array}\right]_2 O-Me$$

| Ex. No. | $R_1$ | $R_3$ | $R_2$ | Me | Melting Point | Estimated Purity % |
|---|---|---|---|---|---|---|
| 73 | " | $CH_3$ | 3,5-di-tert-butyl-4-hydroxyphenyl | Co | >240° | 90–95 |
| 74 | " | phenyl | 4-tert-butylphenyl | Co | ~225° | 98–100 |
| 75 | " | $CH_3$ | 4-methoxyphenyl | Co | ~205° | 98–100 |
| 76 | " | $C_3H_7$ | phenyl | Co | 160–175° | 98–100 |
| 77 | 4-methylphenyl | $CH_3$ | $-C_{11}H_{23}$ | Co | 110–115° | 95–98 |
| 78 | phenyl | " | 4-methoxyphenyl | Mn | 175–180° | 98–100 |
| 79 | " | " | $-CH_3$ | Mn | 185–195° | 95–98 |
| 80 | " | " | $-C_9H_{19}(n)$ | Mn | 123–138° | 95–98 |
| 81 | " | " | 5-methyl-2,3-dichloroquinoxalinyl | Mn | 220–225° | 95–98 |
| 82 | " | " | cyclohexyl | Co | ~190° | 98–100 |
| 83 | 4-methylphenyl | " | $-C_{11}H_{23}$ | Ni | 140–145° | 98–100 |
| 84 | phenyl | $C_3H_7$ | phenyl | Ni | 155–160° | 98–100 |
| 85 | " | $CH_3$ | $-C_7H_{15}$ | Ni | ~140° | 98–100 |
| 86 | " | " | 4-tert-butylphenyl | Ni | >250° | 98–100 |
| 87 | phenyl | $CH_3$ | phenyl | Zn | 185–190° | 98–100 |
| 88 | " | " | 4-methoxyphenyl | Zn | 180–185° | 98–100 |
| 89 | " | " | $CH_3$ | Zn | 175–180° | 95–98 |
| 90 | " | " | $-C_9H_{19}(n)$ | Zn | 145–150° | 95–98 |

Table 3-continued

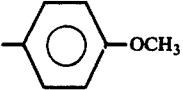

| Ex. No. | $R_1$ | $R_3$ | $R_2$ | Me | Melting Point | Estimated Purity % |
|---|---|---|---|---|---|---|
| 91 | " | " | 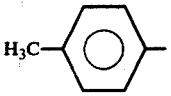 | Ca | >200° | 98-100 |
| 92 | " | 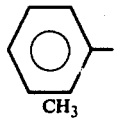 | 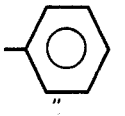 | Ca | 200-205° | 98-100 |
| 93 | 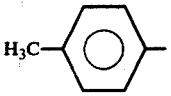 | $CH_3$ | " | Ca | >250° | 98-100 |
| 94 | " | " |  | Ca | 205-220° | 98-100 |

Table 4

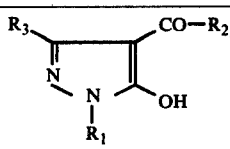

| Ex. No. | $R_1$ | $R_3$ | $R_2$ | Melting Point | Estimated Purity % |
|---|---|---|---|---|---|
| 95 | 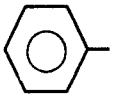 | $CH_3-$ | 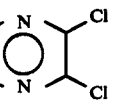 | 149-151° | 98-100 |

Table 5

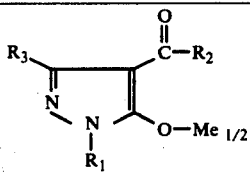

| Ex. No. | $R_1$ | $R_3$ | Me | $R_2$ | Melting Point | Estimated Purity % |
|---|---|---|---|---|---|---|
| 96 | 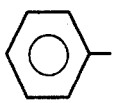 | $CH_3$ | Zn | 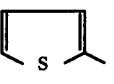 | 190-195° | 95-98 |
| 97 | " | " | Mn | " | 180-190° | 95-98 |
| 98 | " | " | Cu | " | 235° | 95-98 |
| 99 | " | $nC_3H_7$ | Mn | " | 130-132° | 95-98 |
| 100 | " | " | Zn | " | 140-145° | 95-98 |
| 101 | " | $CH_3$ | Mn | " | 175-180° | 95-98 |
| 102 | 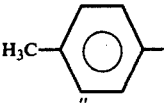 | " | Zn | " | 180-185° | 95-98 |

For each of the tabulated examples above the final isolated product was submitted to a conventional purification procedure, e.g. washing with water and/or methanol, and, in many cases, recrystallization, e.g. from methanol. The purity was estimated from considerations of the estimated purities of the appropriate starting 1,3-disubstituted pyrazole, acid chloride and salt, of the physical state of the product, the breadth of the melting range where over more than one Centigrade degree, of the results of elemental analysis and infra-red spectroscopy, and of the expectation that only a single product would be produced from the starting materials employed.

All the metal complex compounds were found to be solid and crystalline, and to have up to 2 moles of water of crystallization associated per mole of product.

Table 6

| Example No. | $R_1$ | $R_3$ | $R_2$ |
|---|---|---|---|
| 103 | H₃C—⟨phenyl⟩— | $CH_3$ | ⟨cyclohexyl⟩—H |
| 104 | ⟨phenyl⟩— | $nC_3H_7$— | ⟨cyclohexyl⟩—H |
| 105 | " | ⟨phenyl⟩— | ⟨thienyl⟩—S |
| 106 | " | " | H₃C—⟨thienyl⟩—S |
| 107 | " | " | Cl—⟨benzothienyl⟩ |
| 108 | H₃C—⟨phenyl⟩— | $CH_3$— | ⟨quinoxalinyl-Cl,Cl⟩ |
| 109 | ⟨phenyl⟩— | $nC_3H_7$— | " |

Table 7

| Example No. | $R_1$ | $R_3$ | $R_2$ | Me |
|---|---|---|---|---|
| 110 | ⟨phenyl⟩— | $nC_3H_7$— | $nC_{11}H_{23}$— | Mn |
| 111 | " | " | " | Zn |
| 112 | " | " | " | Ni |
| 113 | " | " | ⟨phenyl⟩—C(CH₃)₃ | Mn |
| 114 | " | " | " | Ni |
| 115 | " | " | ⟨cyclohexyl⟩—H | Zn |
| 116 | " | " | " | Co |

Table 7-continued $$\left[\begin{array}{c} R_3 \quad CO-R_2 \\ \diagdown \\ N \\ \| \\ N \\ | \\ R_1 \end{array} O-C(Me)\right]_2$$

| Example No. | $R_1$ | $R_3$ | $R_2$ | Me |
|---|---|---|---|---|
| 117 | " | $CH_3$ | $C_{13}H_{27}-$ | Cu |
| 118 | " | " | $C_{15}H_{31}-$ | Cu |
| 119 | " | " | $C_{17}H_{35}-$ | Cu |
| 120 | " | " | 2-thienyl | Ca |
| 121 | " | $nC_3H_7-$ | " | Cr |
| 122 | 4-tolyl | $CH_3$ | " | Cr |
| 123 | " | phenyl | " | Ni |
| 124 | " | " | " | Mn |
| 125 | $CH_3$ | $CH_3$ | " | Ni |
| 126 | " | " | " | Cr |
| 127 | phenyl | " | " | Ni |
| 128 | " | " | 2,5-dimethyl-3-thienyl | Cr |
| 129 | " | " | " | Mn |
| 130 | " | " | " | Ni |
| 131 | " | " | 3-chloro-2-benzothienyl | Mn |
| 132 | " | $nC_3H_7-$ | " | (2) H |
| 133 | " | " | " | Ni |
| 134 | " | " | " | Mn |
| 135 | " | $CH_3$ | 6-methyl-2,3-dichloroquinoxalinyl | Ni |
| 136 | " | " | " | Zn |
| 137 | 4-tolyl | " | " | Ni |
| 138 | " | " | " | Zn |
| 139 | " | " | " | Mn |
| 140 | phenyl | " | " | Ni |
| 141 | " | " | " | Zn |
| 142 | $CH_3$ | " | " | Ni |
| 143 | 4-tolyl | " | 4-tert-butylphenyl | Ni |
| 144 | " | " | cyclohexyl | Zn |
| 145 | " | " | " | Co |
| 146 | phenyl | phenyl | phenyl | Mn |

Table 7-continued

| Example No. | R₁ | R₃ | R₂ | Me |
|---|---|---|---|---|
| 147 | H₃C—⟨C₆H₄⟩— | CH₃ | " | Mn |

For each of the examples in Tables 6 and 7 above the product would be expected to have a purity of at least 90%, excluding water of crystallization, after submission to a conventional purification procedure, e.g. washing with water and/or methanol, and optionally recrystallization, e.g. from methanol.

EXAMPLE 148

34.8 parts of 1-phenyl-3-methyl-pyrazolone (5) and 13.2 parts of CaO are entered into 40.0 parts of dioxan at room temperature. The mixture is then heated in an oil bath to 80° C. At 75° C., 38.0 parts of capric acid chloride is added dropwise with stirring over a period of 45 minutes. The temperature increases to 95° C. to result in a thick brown, well-stirrable paste. After the addition of the acid chloride, the mixture is allowed to further react at 80° C. for 1 hour. The mixture is then cooled to 50° C., 100 ml of methanol and 23.0 parts of hydrochloric acid are added thereto and the mixture is stirred for 30 minutes. 24.8 parts of nickel acetate are then transferred to the mixture and stirring is effected for 30 minutes at 70° C. The precipitated nickel complex is filtered off at 50° C., washed three times with 30 parts of methanol, four times with 20 parts of water and lastly three times with 30 parts of methanol, and dried at 110° C. When the above procedure is followed, a product is obtained having between 0 and 2 mols of water of crystallization and being in accord with the following formula

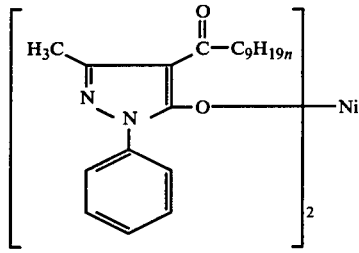

Melting point 158°–162° C. The estimated purity of the product was 98–100%.

EXAMPLE 149

131.8 parts of 1-phenyl-3-methyl-pyrazolone (5) and 49.5 parts of calcium oxide are added to 400 parts of dioxan at room temperature. To the resulting suspension are then added with stirring 8.2 parts of lauryl chloride, after which the mixture is heated to 92°–96° and a further 155.8 parts of the acid chloride are added over a period of one hour. To the resulting brown suspension are added successively 60 parts of water and 78.5 parts of concentrated hydrochloric acid, and the mixture is stirred for 30 minutes. The aqueous phase is then separated and the dioxan solution distilled to afford an oil. To the latter at 90° are added 500 parts of methanol, and the resulting methanolic solution at 45°–55° is treated with 78.4 parts of nickel acetate tetrahydrate. The mixture is stirred for 30 minutes, whereafter the precipitate formed is collected by vacuum filtration at 40°. After washing first with 620 parts of methanol in 5 portions and then with 500 parts of water in 4 portions the salt is dried at 85°–90° C. at 15 mm of mercury pressure to constant weight. There are obtained 247 parts of the compound of formula,

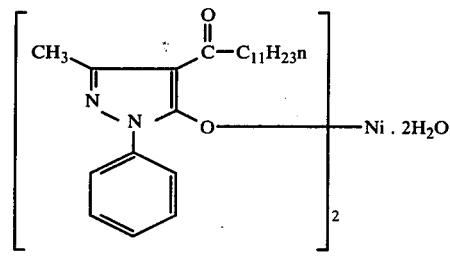

as a blueish green powder, melting point 140°–155° C. and having an estimated purity of 98–100%.

METHOD EXAMPLE 4 samples of unstabilized polypropylene and 0.5% by weight of the compound of Example numbers 25 (Table 1) and 32 and 47 (Table 2) and of the compound of Example 9, respectively, are intimately kneaded on a roll mill at 180°. Each sample is extruded into sheets of 0.3 mm thickness. Specimens of the sheets were tested for stability in the "Klimatest" apparatus by the De La Rue method at 40° and 75% relative atmospheric humidity, with thorough ventilation and irradiation by 16 sun lamps and 16 black lamps of Philips manufacture. Specimens of an unstabilized polyvinyl chloride sheet and a sheet containing 0.5% of the compound of Example 17 in Table 1 were tested in analogous manner in the "Klimatest" apparatus.

Analogous results are obtained for polyethylene, acrylonitrile-butadiene-styrene terpolymers, polyethylene terephthalate, cellulose acetobutyrate, polyamide 6, polystyrene, polycarbonate and polyurethane.

What is claimed is:

1. A compound of the formula:

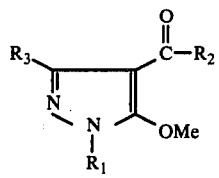

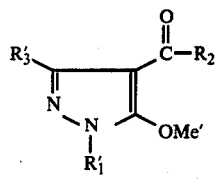

wherein
Me is an equivalent of nickel, zinc, manganese, copper, chromium, calcium, barium or cobalt, $R_1$ is $(C_{1-22})$ alkyl; $(C_{5-12})$ cycloalkyl; $(C_{5-11})$ cycloalkyl $(C_{1-7})$ alkyl; $(C_{1-21})$ alkyl $(C_{1-21})$ thioalkyl with $C_2$-$C_{22}$ in the aggregate thereof; $(C_{5-11})$ cycloalkyl $(C_{1-6})$ alkyl $(C_{1-6})$ thioalkyl with $C_7$-$C_{18}$ in the aggregate thereof; $(C_{7-12})$ aralkyl; $(C_{7-12})$ aralkyl substituted on the aryl nucleus, wherein each substituent is, independently, selected from hydroxy, $(C_{1-12})$ alkyl, $(C_{5-12})$ cycloalkyl and $(C_{5-11})$ cycloalkyl $(C_{1-11})$ alkyl, with the proviso that the maximum number of hydroxy or $(C_{1-12})$ alkyl groups is 2, and the maximum number of each of the remaining substituents is 1; phenyl, substituted phenyl, wherein each substituent of substituted phenyl is, independently, selected from halo, cyano, hydroxy, $(C_{1-12})$ alkyl, $(C_{1-12})$ alkoxy, phenyl, $-SO_3H$ and a radical $R_4-O-$ or a radical $R_4-SO_2-$, wherein $R_4$ is phenyl or phenyl substituted by 1 or 2 $(C_{1-8})$ alkyl groups, with the proviso that the maximum number of halo atoms is 3, the maximum number of hydroxy, $(C_{1-12})$ alkyl or $(C_{1-12})$ alkoxy groups is 2, the maximum number of $R_4-O-$ and $R_4-SO_2-$ radicals together is 1, and the maximum number of each of the remaining substituents is 1;

$R_2^{IV}$ is $(C_{8-18})$ alkyl; $(C_{6-12})$ cycloalkyl; $(C_{7-10})$ aralkyl; $(C_{7-10})$ aralkyl monosubstituted on the aryl nucleus by hydroxy; $(C_{7-10})$ aralkyl monosubstituted on the aryl nucleus by $(C_{1-6})$ alkyl; $(C_{7-10})$ aralkyl disubstituted on the aryl nucleus by $(C_{1-6})$ alkyl; $(C_{7-10})$ aralkyl monosubstituted on the aryl nucleus by hydroxy and monosubstituted on the aryl nucleus by $(C_{1-6})$ alkyl; $(C_{7-10})$ aralkyl monosubstituted on the aryl nucleus by hydroxy and disubstituted on the aryl nucleus by $(C_{1-6})$ alkyl; phenyl; phenyl substituted by one to three substituents selected from 1 or 2 halo atoms, hydroxy, 1 or 2 $(C_{1-8})$ alkyl groups, 1 or 2 $(C_{1-8})$ alkoxy groups and phenyl; furan; thiophene; benzothiophene; indole; pyridine; quinoxaline; or a furan, thiophene, benzothiophene, indole, pyridine or quinolaxine radical substituted by one or two substituents selected from 1 or 2 halo atoms, 1 or 2 $(C_{1-4})$ alkyl groups and 1 or 2 $(C_{1-4})$ alkoxy groups; and $R_3$ has one of the significances of $R_1$ or is cyano; $-COOR_5$, wherein $R_5$ is $(C_{1-12})$ alkyl; $(C_{5-12})$ cycloalkyl; $(C_{5-11})$ cycloalkyl $(C_{1-7})$ alkyl; phenyl; phenyl monosubstituted by hydroxy; phenyl monosubstituted by $(C_{1-8})$ alkyl; phenyl disubstituted by $(C_{1-8})$ alkyl; phenyl monosubstituted by hydroxy and monosubstituted by $(C_{1-8})$ alkyl; or phenyl monosubstituted by hydroxy and disubstituted by $(C_{1-8})$ alkyl;

with the proviso that $R_2^{IV}$ is other than unsubstituted phenyl when $R_1$ is phenyl and $R_3$ is alkyl, in at least 90% by weight pure form.

2. A compound according to claim 1 having the formula, wherein
$R_1'$ and $R_3'$ are each, independently, $(C_{1-8})$ alkyl; phenyl; phenyl monosubstituted by halo; phenyl monosubstituted by $(C_{1-4})$ alkyl; phenyl disubstituted by $(C_{1-4})$ alkyl; phenyl monosubstituted by halo and monosubstituted by $(C_{1-4})$ alkyl; or phenyl monosubstituted by halo and disubstituted by $(C_{1-4})$ alkyl;

Me' is an equivalent of nickel, zinc, manganese, copper, chromium, calcium, barium or cobalt; and $R_2^{IV}$ is as defined in claim 1.

3. A compound according to claim 2 having the formula,

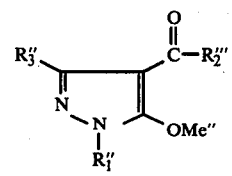

wherein
$R_1''$ is methyl; phenyl; or phenyl monosubstituted by $(C_{1-4})$ alkyl;

$R_3''$ is $(C_{1-4})$ alkyl; or phenyl;

$R_2''''$ is $(C_{8-11})$ alkyl; cyclohexyl; phenylethyl; phenylethyl monosubstituted on the phenyl nucleus by hydroxy; phenylethyl monosubstituted on the phenyl nucleus by hydroxy and monosubstituted on the phenyl nucleus by $(C_{1-4})$ alkyl; phenylethyl monosubstituted on the phenyl nucleus by hydroxy and disubstituted on the phenyl nucleus by $(C_{1-4})$ alkyl; phenylethyl monosubstituted on the phenyl nucleus by $(C_{1-4})$ alkyl; phenylethyl disubstituted on the phenyl nucleus by $(C_{1-4})$ alkyl; phenyl; phenyl substituted by one to three substituents selected from hydroxy, 1 or 2 $(C_{1-4})$ alkyl groups, $(C_{1-4})$ alkoxy and phenyl; furan; thiophene; benzothiophene; or a furan, thiophene or benzothiophene radical substituted by one or two substituents selected from chloro, methyl and ethyl; and Me'' is an equivalent of nickel, zinc, manganese, copper, chromium or cobalt.

4. A compound according to claim 1 having the formula,

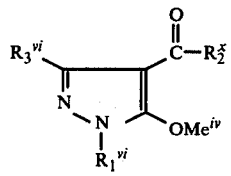

wherein
$R_1^{vi}$ is phenyl; or phenyl monosubstituted by $(C_{1-4})$ alkyl;

$R_3^{vi}$ is $(C_{1-4})$ alkyl;

$R_2^x$ is $(C_{8-17})$ alkyl; phenyl; phenyl monosubstituted by hydroxy; phenyl monosubstituted by hydroxy and monosubstituted by $(C_{1-4})$ alkyl; phenyl monosubstituted by hydroxy and disubstituted by $(C_{1-4})$ alkyl; phenyl monosubstituted by $(C_{1-4})$ alkyl; phenyl disubstituted by $(C_{1-4})$ alkyl; phenylethyl; phenylethyl monosubstituted on the phenyl nucleus by hydroxy; phenylethyl monosubstituted on the phenyl nucleus by hydroxy and monosubstituted on the phenyl nucleus by $(C_{1-4})$ alkyl; phenylethyl monosubstituted on the phenyl nucleus by hydroxy and disubstituted on the phenyl nucleus by $(C_{1-4})$ alkyl; phenylethyl monosubstituted on the phenyl nucleus by $(C_{1-4})$ alkyl; or phenylethyl disubstituted on the phenyl nucleus by $(C_{1-4})$ alkyl; and $Me^{iv}$ is an equivalent of nickel or manganese.

5. A compound of claim 2, wherein Me' is nickel, zinc, manganese, copper, chromium or cobalt.

6. A compound of claim 4, of the formula:

[Structure: H3C-pyrazole ring with N-C6H5, CO-phenyl-C(CH3)3, ONi½]

in at least 95% by weight pure form.

7. A compound of claim 4, of the formula:

[Structure: H3C-pyrazole with N-C6H5, CO-CH2-CH2-phenyl substituted with C(CH3), OH, C(CH3)3, and ONi½]

in at least 95% by weight pure form.

8. A compound of claim 3, of the formula:

[Structure: H5C6-pyrazole with N-C6H5, COC6H5, OMn½]

in at least 95% by weight pure form.

9. A compound of claim 4, of the formula:

[Structure: H3C-pyrazole with N-C6H5, CO-phenyl-C(CH3)3, OMn½]

in at least 95% by weight pure form.

10. A compound of claim 3, of the formula:

[Structure: H3C-pyrazole with N-C6H5, CO-phenyl with C(CH3)3, OH, C(CH3)3, OCo½]

in at least 95% by weight pure form.

11. A compound of claim 4, of the formula:

[Structure: H3C-pyrazole with N-(p-tolyl), CO-phenyl, OMn½]

in at least 95% by weight pure form.

12. A compound of claim 4, of the formula:

[Structure: H3C-pyrazole with N-(p-tolyl), CO-C11H23(n), ONi½]

in at least 95% by weight pure form.

13. A compound of claim 4, of the formula:

[Structure: H3C-pyrazole with N-C6H5, CO-C8H17(n), ONi½]

in at least 95% by weight pure form.

14. A compound of claim 4, of the formula:

[Structure: H3C-pyrazole with N-C6H5, COC11H23, ONi½]

in at least 95% by weight pure form.

15. A compound of claim 4, of the formula:

[Structure: H3C-pyrazole with N-C6H5, COC17H35, ONi½]

in at least 95% by weight pure form.

16. A compound of claim 4, of the formula:

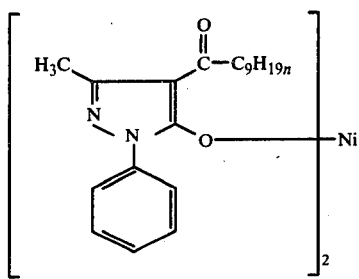

in at least 95% by weight pure form.

17. A compound of claim 4, wherein $R_2^X$ is alkyl($C_{8}$-$C_{17}$).

18. A compound of claim 17 in 95–100% by weight pure form.

19. A compound of claim 18 in 98–100% by weight pure form.

20. A compound of claim 17, wherein $R_1^{VI}$ is phenyl, $R_2^X$ is ($C_{8-13}$) alkyl, and $R_3^{VI}$ is methyl, in 95–100% pure form.

21. A compound of claim 1, in solid form.

22. A compound of claim 1, in crystalline form.

23. A compound of claim 22 having 1 or 2 moles of water of crystallization associated with each mole of compound.

* * * * *

UNITED STATES PATENT AND TRADEMARK OFFICE
CERTIFICATE OF CORRECTION

PATENT NO. : 4,146,540
DATED : March 27, 1979
INVENTOR(S) : Lajos Avar/Kurt Hofer/Martin Preiswerk It is certified that error appears in the above-identified patent and that said Letters Patent are hereby corrected as shown below:

Claim 1, Col. 33, in the structural formula; change "$R_2$" to --$R_2^{IV}$--.

Claim 1, Col. 33, in the definition of $R_2^{iv}$, line 16; change "quinolaxine" to --quinoxaline--.

Claim 2, Col. 34, in the structural formula; change "$R_2$" to --$R_2^{IV}$--.

Claim 3, Col. 34, line 2 beneath the structural formula; change "$R_1'$" to --$R_1''$--.

Claim 3, Col. 34, line 4 beneath the structural formula; change "$R_3'$" to --$R_3''$--.

Col. 38, claim 17, line 2; change "$C_{8-c17}$)" to --$C_8-C_{17}$)--.

Signed and Sealed this

Nineteenth Day of February 1980

[SEAL]

Attest:

SIDNEY A. DIAMOND

Attesting Officer    Commissioner of Patents and Trademarks